United States Patent [19]
Budny

[11] Patent Number: 5,871,714
[45] Date of Patent: Feb. 16, 1999

[54] COMPOSITIONS FOR CONTROLLING BACTERIAL COLONIZATION

[75] Inventor: John A. Budny, Westlake Village, Calif.

[73] Assignee: PharmaCal Biotechnologies, Inc., Westlake Village, Calif.

[21] Appl. No.: 951,393

[22] Filed: Oct. 16, 1997

[51] Int. Cl.⁶ .............................. A61K 7/16; A61K 7/28; A61K 38/00; A61K 31/70
[52] U.S. Cl. .................. 424/49; 424/50; 514/2; 514/23
[58] Field of Search ............................ 424/49, 50; 514/2, 514/23

[56] References Cited

U.S. PATENT DOCUMENTS

| | | |
|---|---|---|
| 3,927,200 | 12/1975 | Yoshimura . |
| 3,952,092 | 4/1976 | Bowen . |
| 4,138,476 | 2/1979 | Simonson . |
| 4,335,101 | 6/1982 | Stoudt . |
| 4,353,891 | 10/1982 | Guggenheim . |
| 4,438,093 | 3/1984 | Shimada . |
| 4,725,428 | 2/1988 | Miyahara . |
| 4,737,359 | 4/1988 | Eigen . |
| 5,085,851 | 2/1992 | Okada . |
| 5,202,113 | 4/1993 | London . |
| 5,290,916 | 3/1994 | Matsushiro . |
| 5,320,831 | 6/1994 | Majeti . |
| 5,362,480 | 11/1994 | Au . |
| 5,409,902 | 4/1995 | Carson . |
| 5,490,978 | 2/1996 | Spaltro . |
| 5,490,988 | 2/1996 | Beggs . |

*Primary Examiner*—Kevin E. Weddington
*Attorney, Agent, or Firm*—Colin P. Abrahams

[57] ABSTRACT

A composition for controlling bacterial growth/colonization is provided. The composition comprises an enzyme, an anchor molecule coupled to the enzyme to form an enzyme-anchor complex, with the anchor being capable of attaching to a substrate proximal to a bacterial colony. The attachment to the substrate permits prolonged retention time of the enzyme-anchor complex where the bacterial colony is present to increase the effectiveness of the complex. The invention is also for a method of controlling colonization of bacterial plaque in the oral cavity, as well as a method of forming a composition for controlling the proliferation of bacterial colonies in the oral cavity.

35 Claims, 1 Drawing Sheet

COMPOSITIONS FOR CONTROLLING BACTERIAL COLONIZATION

FIELD OF THE INVENTION

The invention relates to compositions for controlling bacterial colonization, particularly, but not restricted to, an oral application for reducing dental plaque. The invention is also for an oral therapeutic treatment which will limit or restrict the extent of bacterial colonization in the oral cavity thus reducing the quantity of dental plaque. By controlling the extent or size of plaque structures with enzymes, bacterial colony proliferation and their invasion into gingival tissue can be limited. The invention also relates to methods of manufacturing such compositions.

BACKGROUND OF THE INVENTION

Periodontal disease is one of the oldest and most common diseases of man. It is apparent in human fossil remains and occurs in otherwise healthy individuals. Today, periodontal disease represents a major worldwide health problem. The disease is a result of the accumulation of dental plaque at the gingival margin. There are two broad classes of periodontal disease which roughly approximates the degree or severity of the pathology: gingivitis and periodontitis.

Gingivitis is an inflammation of the marginal gingival tissue due to the accumulation of dental plaque. For the most part, gingivitis is characterized by redness, swelling and bleeding of the gingival tissue. The extent and severity of these characteristics indicate the degree to which the disease has progressed. Periodontitis is characterized not only by the inflammation of the marginal gingivae, but also by loss of the attachment of the periodontal ligament, loss of alveolar bone and loss of the epithelial attachment due to apical migration. The pathological consequences of these physiological losses is the formation of a periodontal pocket, which can become infected, and thus be the source of bacterial infiltration into the host. The progression of established gingivitis to an advanced lesion may well lay the foundation for periodontitis.

The literature indicates that there are significant microbial population shifts from sites of gingival inflammations to subgingival pockets. Certain identified and specific bacterial organisms are known to be responsible for periodontal disease in humans; however, other organisms may also contribute to the severity of the disease. In addition, results from clinical studies show a correlation between the presence of certain microbial species and different types and degrees of severity of periodontal disease. There is a cause-and-effect relationship between the presence and quantity of plaque, containing a wide variety of colonized bacterial strains, and periodontal disease. It therefore follows that, by limiting plaque, the extent and severity of periodontal disease can be controlled.

Both chronic gingivitis and chronic periodontitis share two important characteristics which may be the clue to their sequential relationship. Both conditions are usually painless until their more advanced stages and both pathologies have an absolute requirement for bacterial plaque before the sequence of these conditions progress and develop into advanced periodontal disease. While there are secondary systemic and external factors which affect the extent the disease, the most important factor, and one that provides the greatest promise of being controllable, is the relationship between bacterial plaque and periodontal disease.

The disease begins its progression through an accumulation of bacterial plaque at the gingival margin. As the pathology progresses, there is chronic inflammation of the gingiva and periodontal ligament, with subsequent degeneration of various gingiva-tooth structures. The chronic inflammation is exacerbated by calculus formed from mineralized plaque at the various tissue interfaces and in the periodontal pocket. Epithelial tissue migration into inflamed and necrotic areas can engulf plaque structures, resulting in abscesses accompanied by purulent exudate. The final and most severe stage of periodontal disease is the resorption of alveolar bone and the eventual exfoliation of the tooth.

Plaque is a heterogeneous mixture of bacterial aggregations embedded in a sticky matrix. While bacterial composition of plaque ranges from 50 to 70 percent, the matrix is derived from dead cells, salivary glycoproteins and serum proteins that are laid on a polysaccharide backbone. The bacteria synthesize the polysaccharides for the plaque backbone as a step in their own colonization process. In addition to the viable bacteria and the matrix, plaque also contains food debris, small numbers of epithelial cells, white blood cells and various other components which are derived from the host and the host's activities.

The formation and development or proliferation of plaque occurs in two stages. The first step may require a base layer of salivary glycoproteins on the tooth's surface as well as on the soft tissue in the oral cavity. This base organic layer, derived from saliva, is adsorbed onto the surface and forms an acquired pellicle. This insoluble acquired pellicle serves as the foundation for supragingival plaque. The second step is the bacterial colonization by "pioneering" bacteria of the acquired pellicle. Once the bacteria have attached to the surface of a structure, they aggregate, develop colonies and plaque begins to form.

There are well over 100 different bacterial species in various dental plaques. This variation in the types of bacteria is influenced by diet, salivary components and bacterial interactions, to name a few. The location of the plaque in the oral cavity, the time of the day, age of the patient and the status of the general oral hygiene of the patient all contribute to the implications and consequences of dental plaque and periodontal disease. Consequently, it is not surprising that plaque is a heterogeneous collection of bacterial communities attached to the tooth providing a vast array of biochemical and physiological consequences. Two major pathological conditions as consequences are periodontal disease and dental caries.

Enzymes as therapeutic agents present unique possibilities. However, some of the early oral pathology research using enzymes was based on the assumption that they would be bactericidal to colonies of organisms found in plaque and therefore would act as "disinfectants". This approach, however, was not fruitful. Recently, it was shown that treatment of buccal epithelial cells with protease altered bacterial adhesion; however, this treatment also distorted the ratios of various bacterial populations. More promising results were obtained when the focus was shifted from bactericidal action to altering plaque formation. These latter results were seen in vitro and in vivo as well as in animal models and human in clinical trials. However, these approaches also fell short of desired therapeutic effectiveness most likely because the required time for an effective action exceeded the retention time of the enzyme in the oral cavity. In short, salivary flow, other fluid and food movement and normal mechanical agitation in the oral cavity reduced the retention time of the enzyme(s). These factors shortened the residence time of the enzymes, resulting in less than desirable clinical efficacy.

When enzymes were tested in vitro, the importance of residence time within the oral cavity was not identified as an important issue. There is no indication that the design of these in vitro studies even identified this important variable. These in vitro systems, that demonstrated activity of enzymes in reducing plaque, did, however, identify other important factors. These other factors included: (1) possibly more than one enzyme may be necessary; (2) greater specific activity of the enzyme may be required; (3) a more appropriate enzyme may be required; or (4) a combination of enzymes may be more effective.

Plaque itself is an extremely complex mixture of various components, namely, macromolecules, living and dead cells (whole bacteria and sloughed epithelial cells from the host), cell fragments and various other contributions of material from both the host and the bacterial flora. The pioneering work on the chemical aspects of plaque focused on the carbohydrate or polysaccharide (PS) backbone of plaque. This was an ideal place to start because the PS backbone not only served as a structural element for the plaque matrix, but it also served as a carbohydrate food-store for the growing colonies of bacteria. Most of the research on PS was centered around determining the properties and structure of glucans; however, there are many other components that form the composition of plaque. In reviewing the scientific literature describing previous dental therapeutic research involving enzymes, certain patterns emerge. Most of the enzyme research to control plaque was conducted under the aegis of caries prevention; however, it is well established that plaque control is a fundamental issue related to both caries prevention and the prevention of periodontal disease. The types of investigations carried out included in vitro examination of bactericidal effects, animal studies and clinical investigations involving human experimentation. Furthermore, most of the clinical studies used a mouthwash as the vehicle to deliver the enzymes, while fewer studies used chewing gum.

U.S. Pat. No. 4,138,476 (Simonson) teaches of plaque dispersing enzymes as oral therapeutic agents by molecular alteration. A glucanohydrolase is combined with a phosphate carrier group such that the enzyme itself has increased affinity for the surfaces of the teeth. The modified glucanohydrolase enzyme covalently crosslinks with the carrier, in the presence of a reacting agent such as ethyl chloroformate, and has an increased binding capacity to hydroxyapatite components of the teeth.

U.S. Pat. No. 5,490,988 (Beggs) relates to the delivery of therapeutic agents to a target site. The patent teaches a highly specific process whereby an antibody fragment is able to bind to a target site through antigen-antibody binding, and provides for a therapeutic agent to be connected onto the antibody fragment through an additional peptide appended to the antibody fragment. The product is thus constituted by the antibody fragment, the peptide and the agent.

Examination of the published clinical protocols for evaluating enzymes shows that there were two reasons why the selected enzymes did not completely exert their desired effects, even though limited clinical efficacy was seen:

a. the enzymes were not modified so that they would be held in the oral cavity for an extended period of time; and b. the oral rinsing was done for various durations and various selected times during the day without particular attention to dosing just prior to a time of limited oral activity (swallowing, chewing and saliva generation, etc.) like sleeping.

SUMMARY OF THE INVENTION

A principal aspect of the invention lies in two concepts, both of which are necessary for a successful therapy for the prevention of periodontal disease. The first of these is the regulation of the amount and architecture of the plaque structure within the oral cavity by using enzymes; the second is the means of retaining the enzymes in the oral cavity. Both of these concepts must preferably be implemented for effective control of periodontal disease to occur.

In one aspect, the present invention modifies selected enzymes in a manner that they will have the capability of limiting plaque or its components. The enzymes selected are preferably ones that specifically degrade polysaccharides. In this way, the backbone structure of the plaque matrix may be limited without either selective or broad-spectrum kill of bacteria, thus avoiding any bacterial imbalances.

The invention provides for the selective control of proliferative bacterial colonization and is, therefore, aimed at prevention rather than treatment. The invention is not dependent upon bactericidal activity in the oral cavity which eliminates (a) potential imbalances in normal bacterial populations e.g., overgrowth either in the oral cavity or at other, remote locations in or on the host; (b) the requirement for considering systemic responses of the host which can be either immunologic and toxic; and (c) the need for delivering the active agents below the gingival margin. The emphasis is thus on bacterial adhesion, specifically in the oral cavity.

The modified enzyme is preferably be attached to selected "anchor" molecule(s) to be retained in the oral cavity. The retention of the enzymes in the oral cavity is preferably maximized by coupling the enzymes to specific molecules that will adhere to the structures and existing biofilms within the oral cavity. Enzymatic activity should be maintained after the coupling. It is important that the process of connecting the selected enzymes to the specific "anchor" molecules does not wholly destroy the enzymatic activity, although it is possible that such activity may be reduced by reason of the coupling. However, at least a minimum effective amount of enzymatic activity should be present after coupling.

In another aspect, the invention also provides a method to determine the extent to which the selected and modified enzymes inhibit oral bacterial plaque growth in an in vitro test system, and in vivo. The selected enzymes which maintain this enzymatic activity after being coupled or derivatized to "anchor" molecules are suitable for use to inhibit plaque growth.

The product of the invention may, but need not necessarily, take the form of an oral rinse which may be used at bed-time. The modified enzymes in the oral rinse are preferably retained in the oral cavity during a time when salivary and mechanical agitation is low. In addition, the length of retention time (six to eight hours during sleeping) may provide an extended period for the therapeutic enzymes to carry out their desired biochemical reactions.

This invention addresses the paradox with respect to dental plaque: on the one hand, pathogenic factors such as bacteria and plaque are retained in the oral cavity, but, on the other hand, it is difficult to retain potentially therapeutic agents, such as enzymes, in the oral cavity. This paradox may be used to advantage for controlling dental plaque by giving selected enzymes the specific trait that the bacteria use to cause periodontal disease i.e., the ability to adhere to surfaces in the oral cavity. In this invention, significant consideration has been given to the important and necessary idea of increasing retention time in the oral cavity of the antiplaque composition, since it is only by extending the retained time of the composition in the oral cavity that it has the ability to effectively prevent plaque buildup. Where antiplaque compositions spend only a very short duration of time in the oral cavity, their effect is by definition very limiting. For achieving bacterial kill, a short retention time may be adequate; however, with the novel concept of altering and limiting the structural architecture of the bacterial colony growth support media, a longer retention time may be required.

Previous research to reduce or eliminate periodontal disease has, for the most part, been aimed directly at eliminating the bacteria; only little research has been directed at controlling the bacterial environment. The present invention attempts to control bacterial colony growth while at the same time maintaining a balance among the various strains of bacteria in the oral cavity. By controlling the quantity of plaque and limiting the amount of extracellular polysaccharide backbone, the size of the bacterial colonies can be controlled. This control can be achieved through the enzymatic compositions and processes of the invention.

DETAILED DESCRIPTION

Figure 1:
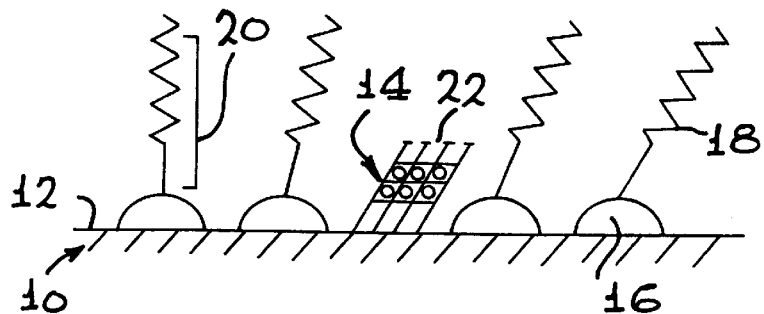
FIG. 1 is a schematic view of the enzyme-anchor complex of the invention, when attached to a tooth.

The present invention proposes to retain selected enzymes in the oral cavity. Unlike incorporating free and nascent enzymes in a dentifrice or oral rinse (where the effects are only transient), enzymes are allowed to have a prolonged opportunity to carry out their desired biochemical reactions and beneficial effects by modifying them so that they can be retained within the oral cavity. In addition, the specific enzymes are preferably selected to minimize toxic responses in the bacteria so as to maintain the normal bacterial balance and at the same time not adversely affect other necessary and protective biofilms, for example, the "acquired pellicle".

Certain polysaccharide degrading enzymes are modified so that they are able to adsorb to surfaces and structures in the oral cavity, and inhibit the proliferative bacterial colonization associated with the plaque matrix. The enzymes are derivatized or coupled to "anchor" molecules. The "anchor" portion of the enzyme-anchor complex can then adhere to structures in the oral cavity, inhibiting the buildup of plaque.

*Streptococcus mutans* and plaque are recognized as being intimately involved in the formation of dental caries. This cariogenic bacterium utilizes sucrose to produce substrates for metabolism for the entire microbial population in the oral cavity. The end products of this sucrose-supported metabolism are organic acids which initiate the sequence of steps involved in the formation of dental caries. In addition, *Streptococcus mutans* also uses sucrose to enhance colonization of the oral flora by using the sucrose-supported substrate pool to produce polysaccharides that are complex and water insoluble. This scenario most likely takes place with many other bacteria that are colonized with the dental plaque.

The insoluble polysaccharide structures provide the backbone for extended bacterial colonization which, when aggregated, is the observable film recognized as plaque. While polysaccharides are not a requirement for initial attachment of the "pioneering" bacteria to the tooth's surface, the colonization and perpetuation of colonies requires these insoluble polysaccharides. It is likely that complex polysaccharides, by their insoluble nature, not only cause colonization and proliferation of the initial bacteria, but may also shield the bacteria from therapeutic agents. Consequently, this invention may be used in conjunction with agents that result in bacterial kill, either specific or non-specific. Restricting and controlling the amount of insoluble polysaccharides, and ultimately bacterial colonization into plaque, has a beneficial effect for the prevention and progression of periodontal disease. One of these complex, insoluble polysaccharides is glucan. The enzymatic degradation of glucan is therefore one of the objects of this invention.

The invention provides for a composition and method to immobilize certain glucan degrading enzymes to surfaces and structures in the oral cavity. This inhibits the buildup of plaque which is a necessary precursor step to periodontal disease. Inhibiting proliferative bacterial colonization may well avoid any distortion of the microbial ecology or balance among the various bacterial strains. In general, avoiding bacterial population shifts is desirable because of the potential for over-growth of opportunistic bacteria, some of which may be pathogenic. The composition of the invention seeks to retain the normal relative ratios of the various bacterial strains in the oral cavity. However, the absolute numbers of at least certain strains of the bacteria will be reduced because the colonies thereof will be smaller.

The development of a mechanism to increase the enzyme's residence time in the oral cavity provides the opportunity for increased clinical efficacy. To achieve this goal, effective enzymes must remain in the oral cavity longer to accomplish their intended action. The increased retention time of the enzymes in the oral cavity will control plaque by limiting the polysaccharide backbone of the plaque matrix.

The composition of the invention is thus designed to facilitate a longer residence time for the enzymes in the oral cavity. This approach involves derivatizing, or coupling, the appropriate enzyme(s) with an "anchor" molecule which will bind to structures in the oral cavity with the "anchor" portion of the derivatized enzyme-anchor complex. The anchor molecule will be specifically chosen to bind to, for example, existing plaque or the acquired pellicle that covers the tooth. Due to the relatively rapid turnover of epithelial tissue, the mucosal tissue layer within the oral cavity is a less preferred choice of a binding site than either the existing plaque or pellicle.

In one embodiment, two enzymes with the type of enzymatic activity that has been shown to be effective in controlling the carbohydrate structural backbone of plaque are connected to three "anchor" molecules. The six resulting enzyme-anchor complexes are tested in an in vitro test system containing saliva (normal bacteria and host glycoproteins) to assess their ability to control plaque and limit its proliferation by binding to the plaque and causing hydrolytic cleavage of the polysaccharide backbone of the plaque. These enzyme-anchor complexes are assessed for clinical efficacy and optimized, as necessary.

Figure 2:
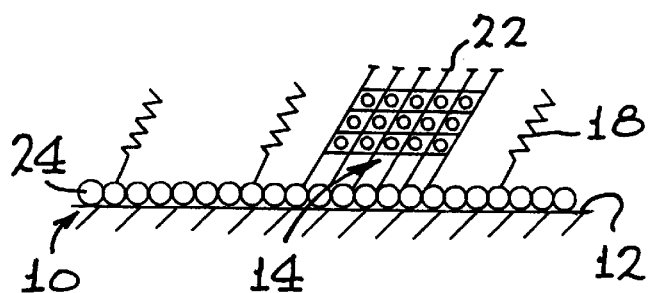
FIG. 2 is a schematic view of the enzyme-anchor complex of the invention, when attached to a pellicle or other surface in the oral cavity.

Reference is made to FIGS. 1 and 2 of the drawings, which schematically illustrate the anchor-enzyme complex of the invention. The drawings are diagrammatic representations, are not intended to be to scale and are for illustrative purposes only. In FIG. 1, there is shown a tooth 10 having a surface 12. On the surface 12, a colony 14 of bacteria within a matrix is attached to the tooth 10. Also attached on the surface 12 of the tooth is an anchor molecule 16, which may be an adhesion peptide. An immobilized enzyme 18 is attached to the anchor molecule 16, and the anchor molecule 16 and immobilized enzyme 18 together form the anchor-enzyme complex 20. The anchor-enzyme complex 20 competes with the colony 14 for attachment to the surface 12 of the tooth 10 and thus reduces the potential substrate sites for colony 14 attachment. Additionally, and most importantly, the enzyme 18 exercises its catalytic effect on the colony 14, degrading the plaque matrix and/or polysaccharide backbone. In FIG. 1, the termination 22 of the matrix by the enzyme 18 can be seen. The colony 14 will thus be severely impaired in its ability to expand. Furthermore, the anchor-enzyme complex 20 has significant retention time on the tooth surface 12, thus providing more than a temporary obstacle to plaque matrix and colony 14 proliferation.

Another embodiment of the invention is shown in FIG. 2. In this figure, elements corresponding to those in FIG. 1 have been accorded the same reference numeral. In the embodiment shown in FIG. 2, the tooth surface 12 has thereon a pellicle 24 to which the enzyme attaches. The pellicle, which includes peptides, proteins and the like, may provide or constitute the anchor, or a separate anchor molecule preattached to the enzyme may be used.

Figure 4:
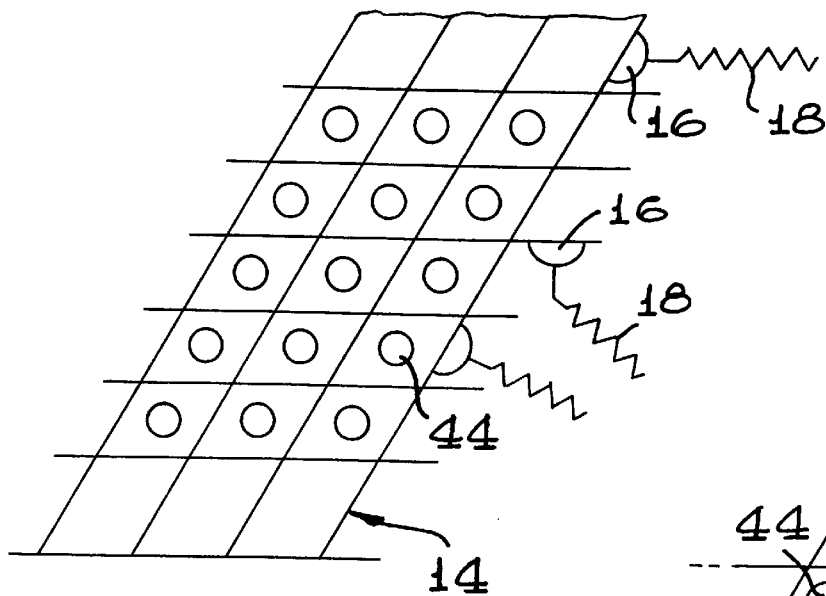
FIG. 4 is a schematic view of the enzyme-anchor complex of the invention, when attached to a bacterial colony matrix in the oral cavity.
Figure 5:
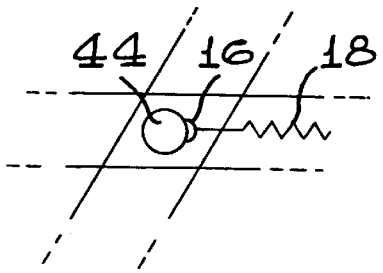
FIG. 5 is a schematic view of the enzyme-anchor complex of the invention, when attached to a bacterium in the bacterial colony matrix in the oral cavity.

In FIG. 4, a detail of a bacterial colony matrix 14 is shown, including individual bacteria 44. In this embodiment, the anchor molecule 16 of the complex 20 attaches to the bacterial matrix, and the termination 22 of the matrix can be clearly seen. In FIG. 5, the anchor 16 of the complex 20 attaches directly on to a bacterium 44 within the matrix 14.

It is within the scope of this invention to expand the enzyme-"anchor" complex to incorporate polysaccharide-degrading enzymes other than those which hydrolyze or degrade glucans e.g., enzymes that degrade fructose-based polysaccharide enzymes that hydrolyze glycoproteins etc. The complex could also extend to cover ligand-based "anchor" molecules that mimic exterior cell surfaces of bacteria so as to create direct competitive binding between bacteria and "anchor" enzyme complexes. Further, the complex may include receptor-based "anchor" molecules that mimic the bacterial attachment sites so that "anchored" enzymes can be adsorbed onto bacterial surfaces that are already adhering to plaque. Finally, anchor molecules comprised of polypeptides that are known adhesion molecules may be used.

Purification of potentially suitable hydrolytic enzymes (polysaccharide hydrolases, glycoprotein degrading enzymes, etc.) may be carried out to achieve higher specific activity and a more focused specific type of reaction.

Thereafter, procedures for determining the extent or degree of coupling between the enzyme and "anchor" molecules may also be carried out, thus establishing the number of "anchor" molecules attached to the enzyme that will provide the best combination of enzymatic activity and degree of binding.

It will be appreciated that any effective enzyme which prevents or reduces bacterial colonization may be used in this invention. Preferably, a group of enzymes which have a hydrolytic action, or hydrolases, are used since they are particularly effective. This group facilitates the hydrolysis of chemical bonds that link moieties, which after the hydrolysis reaction occurs, can exist as separate chemical entities. Preferred enzymes which may be used in this invention may be selected from one or more of the following: esterases—those enzymes that cleave ester bonds; glycolytic cleavage enzymes—those enzymes that cleave bonds that are found in oligo—and polysaccharides; ether bond cleavage enzymes; peptide bond cleaving enzymes where proteins are the substrate (reactant); carbon-nitrogen bond cleavage where the substrate (reactant) is not a protein; acid anhydride cleaving enzymes; carbon—carbon bond cleavage; halide bond cleavage; phosphorus-nitrogen bond cleavage; sulfur-nitrogen bond cleavage; and carbon-phosphorus bond cleavage.

Anchor molecules and structures for anchoring the enzymes in the oral cavity may be selected from a number of different categories, as set out below:

A. proteins, protein fragments and polypeptides
   a. naturally-occurring
   b. naturally-occurring, but modified
   c. synthetic polypeptides
      i. using naturally occurring amino acids
      ii. using synthetic, non-naturally occurring amino acids e.g. D-amino acids, β-substituted amino acids, alpha, alpha-disubstituted etc.
   d. charge prevalence
      i. cationic (basic amino acids)
      ii. anionic (acidic amino acids)
      iii. neutral (aliphatic amino acids)
   e. any combination of the above B. saccharides and oligosaccharides
   a. naturally occurring e.g. glucose, mannose, galactose, rhamnose, fucose, fructose, sucrose etc.
   b. naturally occurring amino sugars e.g. glucosamine, galactosamine, N-actylglucosamine, N-acetylgalactosamine, neuramenic acid, sialic acid, etc.
   c. synthetic or non-naturally occurring saccharides and amino sugars
      i. esters of sugars e.g. sugar-organic acid esters etc
      ii. chemically combined sugars and proteins/polypeptides e.g. synthetic glycoproteins C. Glycoproteins/proteoglycans
   a. naturally occurring e.g. elastin, lectins etc.
   b. synthetic e.g. modified naturally occurring glycoproteins/proteoglycans D. Glycolipids
   a. naturally occurring e.g. sphingomyelin, cerebroside, gangliosides etc
   b. synthetic e.g. modified natural glycol; lipids through some chemical procedure such as esterification, amidation or similar chemical process E. Lipoprotein e.g. chylomicron, Very Low Density Lipoproteins (VLDL), Low Density Lipoproteins (LDL), High Density Lipoproteins (HDL), etc.

F. Lipids
   a. non-polar, natural or synthetic e.g. triglycerides, cholesterol or other plant or animal sterols, etc
   b. polar, natural or synthetic e.g. phospholipids (phosphatidyl serine), etc G. Cell fragments and cell ghosts—segments or portions of exterior bacterial or animal cell walls or membranes that would mimic live and viable bacterial or animal cells for the purpose of securing an enzyme to the surface within the oral cavity.

H. Non-biologic, polymeric materials
   a. homopolymers e.g. polyethylene glycol (PEG), etc
   b. copolymers e.g. styrene-butadiene polymers etc.

Figure 3:
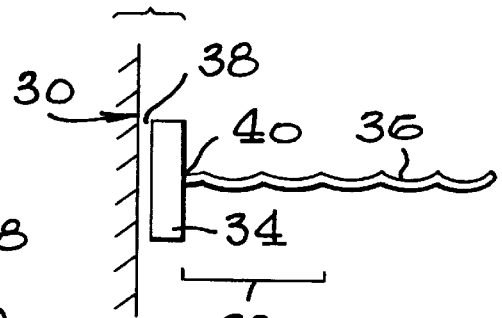
FIG. 3 is a schematic view of a further embodiment of the enzyme-anchor complex of the invention, when attached in the oral cavity.

The connections between the anchor molecules and the enzymes may also take a number of forms. These connections may thus be chemical, chemisorption, or covalent bonds, including: amide (peptide); ester; glycosidic (sugar linkages); and/or ether. The connections may also be physical, physisorption such as: van der Waals attractive forces, including lipophilicity; charge—charge attractions/interactions, including electrostatic interactions; and/or hydrogen bonding, including hydrophilicity The connections between the anchor of the anchor-enzyme complex and the surface substrate within the oral cavity would typically be the same as those listed in the preceding paragraph. With reference to FIG. 3 of the drawings, there is shown in schematic form of a substrate 30 which is a surface in the oral cavity such as a tooth, existing plaque, an appliance or mucosal tissue, and an anchor-enzyme complex 32 attached thereto. The anchor-enzyme complex 32 comprises an anchor portion 34 and an enzyme portion 36. There is an anchor-surface interface 38 between the complex 32 and the substrate 30 and an anchor-enzyme connection 40. It is believed that there will be a greater tendency for the connection between the enzyme portion 36 and the anchor portion 34 to be of the chemical type, while the interaction between the anchor portion 34 of the anchor-enzyme complex 32 and the substrate 30 is more likely to be of the physical type.

There will be a greater tendency for the connection between the enzyme and anchor to be of the chemical type. The interaction of the anchor portion of the anchor-enzyme complex will more likely be of the physical type.

EXAMPLE

An embodiment of the invention involves selection of two enzymes known to have activity on degrading the polysaccharide backbone of the dental plaque matrix. Two such enzymes are:

1) α-Glucosidase EC 3.2.1.20; [(1→3) 3-glucanohydrolase]. α-Glucosidase is commercially available. While the enzyme shows greatest activity toward α-1,4 glucose linkage, it will also hydrolyze α-1,2 and α-1,3 linkages. The enzyme will also hydrolyze α-1,6 linkages, but only at a very slow rate.

2) Dextranase EC 3.2.1.11 ; [(1→6) 6-glucanohydrolase]. Dextranase is also commercially available. This enzyme cleaves glucose molecules from polysaccharides that are linked α-1,6.

Many researchers describe the glucan structure as α-1→3 and α-1→6. Glucan has also been described as having α-1→4 and α-1→2 linkages. From a structural perspective, α-1→6 linkages give the glucan its length and the α-1→3, α-1→4, and α-1→2 linkages gives the glucan its branching characteristics. It is not known whether glucan length or glucan branching is important for bacterial colonization. For this reason, the two commercially available enzymes were selected: α-Glucosidase, providing cleavage activity for α-1→4, α-1→2 and α-1→3 i.e., cleaving at branching points in the glucan structure; and Dextranase, which will provide cleavage of α1→6 linkage i.e., cleavage at lengthening linkages.

These enzymes will be separately coupled with each of the following "anchor" molecules:

1) a basic polypeptide e.g., Lys-Lys-Glu-Lys-Lys or some similar basic polypeptide;

2) an acidic polypetide e.g., Glu-Glu-Lys-Glu-Glu or some similar acidic polypeptide.

Teichoic acids and lipoteichoic are important bacterial cell wall components for binding. These components are also associated with phosphate esters which would present an anionic character to the exterior portion of the bacterial cell surface. For this reason, the "anchor" molecule, Lys-Lys-Glu-Lys-Lys, which is a cationic species, would be attracted to the bacterial cell wall.

Since available evidence suggests that the bacterial cell surface is anionic in character, it is reasonable to suspect the colonization of bacteria on to portions of plaque that are principally cationic in character. Indeed, if there are regions or areas of cationic character associated with plaque, the "anchor" molecule, Glu-Glu-Lys-Glu-Glu, which is an anionic species that would be attracted to the cationic regions of plaque, would be a good choice.

Additionally, or alternately, any other densely arranged lipid character such as micelles may serve as either a substrate in the oral cavity or the anchor molecule to which the enzyme-anchor complex attaches.

The rationale of charge attractions, as the basis for anchoring selected enzymes to various organic structures in the oral cavity, may be one factor for bacterial attachment. However, bacterial adhesion in the colonization of plaque also may involve factors other than charge attraction alone. Thus, specific proteins may be responsible for the binding of oral bacteria to polysaccharide (glucan) and plaque. However, the actual mechanism for bacterial binding in plaque does not preclude other binding mechanisms for enzymes that are connected to specific "anchor" molecules, and would be encompassed by this invention.

The enzymes and anchors set out in this example will produce six derivatized enzymes with the potential for a broad charge-binding capability.

Synthesis

The synthesis part of the derivatized enzyme-anchor complexes involves coupling of each "anchor" molecule to the two individual enzymes. The basic polypeptide Lys-Lys-Glu-Lys-Lys is coupled to the two enzymes through the free carboxyl group of the Glu residue and there is some coupling through the "C" terminus of the polypeptide. The acidic polypeptide Glu-Glu-Lys-Glu-Glu is coupled through the free amino group of the Lys residue and there is some coupling through the "N" terminus of the polypeptide to the two enzymes.

Purification of the six derivatized enzyme reaction products may be carried out by molecular size exclusion on column chromatography. The purified coupled enzymes may be assayed and compared to the underivatized enzymes to determine any changes in enzymatic activity as a consequence of the coupling procedure.

The six anchor-enzyme complexes produced in this example, or complexes of other enzymes and anchors, may further be tested in the in vitro system prior to clinical application. Any suitable procedure for testing may be used, for example, the procedure of Drake [Drake, D. R., Vargas, K., Cardenzana, A. and Srikantha, R. "Enhanced bactericidal activity of Arm and Hammer dental care." *Am. J. Dent.* 8, 308–312 (1995)] or a modification thereof.

The basic and acidic polypeptides, which are commercially available, for example from Peptides International, Louisville, Ky., are synthesized, for example, by a variation of the solid-phase method. These starting materials may be used without purification; however, a retained portion of each starting material should preferably be assayed for purity, as necessary e.g., to describe unexpected reaction products, etc.

The enzymes, which are also commercially available and may be purchased from United States Biochemical, Cleveland, Ohio and Worthington Biochemical, Freehold, N.J., may also be used without purification. Other enzymes which can be used and which may not be commercially available can be isolated and purified from tissues and organisms, using standard procedures. A retained portion of each enzyme, too, should be analyzed, only if necessary to determine purity. Such purification analyses may be important depending upon the results of the in vitro experimentation. These analyses may be conducted using the retained portions of the enzymes.

The enzymatic activity should preferably be determined both before and after the derivatization (coupling) reaction and this can readily be accomplished using, for example, 4-nitrophenyl-α-D-glucose in a standard assay procedure.

The basic polypeptide, Lys-Lys-Glu-Lys-Lys may be coupled to each of the enzymes using a modification of the procedure described by Williams (1981). [Williams, A. and Ibrahim, I. A. "A mechanism involving cyclic tautomers for the reaction with nucleophiles of the water-soluble peptide coupling reagent 1-ethyl-3-[-3-dimethylaminopropyl]-carbodiimide (EDC)." *J. Am. Chem. Soc.* 103, 7090–7095 (1981)]. This procedure uses 1-ethyl-3-[-3-dimethylaminopropyl]-carbodiimide (EDC) as the coupling agent. The EDC-activated carboxyl group of Glu in the polypeptide (as well as the carboxyl group from the "C" terminus end of the polypeptide) will be coupled to free amine groups on the enzymes, forming covalent amide bonds.

The acidic polypeptide, Glu-Glu-Lys-Glu-Glu, may be coupled to each of the enzymes using a modification of the procedure described by O'Shannessy (1987). [O'Shannessy, D. J. and Hofmann, W. L. "Coupling antibodies for site directed immobilization." *Biotech. Appl. Biochem.* 9, 488–496 (1987)]. In this procedure, the free amine group of Lys (as well as the free amine group from the "N" terminus of the polypeptide) is converted to an aldehyde and then coupled to the free amine groups on the enzymes.

In both of the coupling or derivativization reactions involving the polypeptide "anchor" molecules, there will be a wide variety of by-products produced; however, there will also be a wide diversity among the sizes of the molecules (molecular weights) which will allow a clean-up procedure using, for example, HPLC with a 3000 PW column for a separation based on molecular size.

The purpose of this separation step is a "clean-up" of the reaction. The clean-up removes unreacted polypeptide "anchor" molecules, polypeptide mixtures resulting from the "anchor" molecules that reacted with each other, and the desired product of enzyme-"anchor" complexes. There may also be a number of desired enzyme-"anchor" complexes, depending upon the number of "anchor" molecules attached to the enzyme. It is not considered necessary to separate enzyme-"anchor" complexes into discrete fractions depending upon the number of "anchor" molecules; rather, all types of enzyme-"anchor" complexes may be tested and clinically applied collectively. Separating the types of enzyme-"anchor" complexes into discrete molecular entities may, however, be carried out where it is considered appropriate.

Where desired or considered necessary, the clean up procedure may be validated by defining and setting the column (HPLC) operating conditions. Sample runs may be made with: 1) the enzyme alone; 2) the anchor molecule alone; and 3) the reaction mixture without the addition of enzyme. Retention time/fraction number for total protein will be determined under the defined operating conditions that will allow separation of free "anchor" molecules, reaction products among "anchor" molecules, free enzyme and derivatized or coupled enzymes.

In Vitro Assay

Prior to clinical application, the effectiveness of any synthesised enzyme-anchor complexes may be determined in an in vitro assay. One such assay is described below.

Subjects are screened for salivary output and a high level of *Streptococcus mutans* and *Actinomyces viscosus* (plate counts) which are recognized as high plaque-forming bacteria. Salivary output from the selected population may be stimulated by chewing an inert material such as parafilm or carbowax. The collected saliva will serve as the stock inoculum solution. This stock solution will be prepared by combining the saliva samples with the greatest population of the identified stains (20–25% of the total samples taken).

Thereafter, the following solutions are prepared:
a) Enriched Sucrose Broth.
b) Positive control solution of 20 mg/ml of chlorhexidine, a known inhibitor of plaque formation.
c) The two test-related controls may be the underivatized enzyme i.e., enzymes without "anchor" molecules.
d) The 8 treatment solutions (6 test solution and 2 test-related controls) may be prepared with Enriched Sucrose Broth as the solvent, giving stock solutions with concentrations of 10, 1.0, and 0.1 mg/ml.

Procedure

Sterile glass slides are placed in 50 ml test tubes containing 39 ml of Enriched Sucrose Broth. The tubes are inoculated with 1 ml of stock inoculum (saliva) solution. The tubes are incubated at 37° C. under 5% $CO_2$ for 24 to 48 hours, until visual evidence of plaque formation appears. The slides are removed, transferred to dosing solutions of fresh Enriched Sucrose Broth (39 ml in 50 ml test tubes) to which 1 ml of the appropriate test solution is added. The dosing solutions may have the following composition:
1) No treatment control—Enriched Sucrose broth
2) Positive control—20 mg/ml chlorohexidine
3) Control related to treatments 1A, 1B and 1C—1.0 mg/ml un-"anchored" α-Glucosidase
4) Control related to treatments 2A, 2B and 2C—1.0 mg/ml un-"anchored" Dextranase
5) Test treatments 2A, 2B and 2C (3 Dextranase-"anchor"): 10, 1.0 and 0.1 mg/ml.
6) Test treatments 2A, 2B and 2C (3 Dextranase-"anchor"): 10, 1.0 and 0.1 mg/ml.

The glass slides remain in their respective dosing solutions for approximately one hour. They are then removed and rinsed by dipping in a clean Enriched Sucrose Broth.

The slides may then be placed in fresh Enriched Sucrose Broth and the tubes incubated in the same manner for 24 to 48 hours. The amount of plaque is recorded (photographed) for each treatment and the plaque from each slide is harvested, dried and weighed.

The enzymatic activity of both enzymes before and after the derivatization is determined, as well as the efficiency of the reaction clean-up. Visual observation is made of each test; photographs are taken of each treatment (combined triplicate test of each treatment as a single photograph), and the amount (weight) of plaque formed in each test is determined.

In the selection of enzymes, anchors and the coupling methods and procedures, a number of factors should be taken into account to provide the most effective enzyme-anchor complexes. Some of these are as follows: The enzymes and anchor molecules selected should always be the most appropriate for limiting a bacterial colonization matrix. More than one enzyme may be necessary to cause a critical limitation of the polysaccharide backbone for plaque formation.

The potential advantages of this invention are threefold: 1) it does not require bactericidal activity, 2) normal microbial balance in the oral cavity will be maintained, and 3) the likelihood of adverse effects in the host at sites removed from the oral cavity are minimized or eliminated.

I claim:

1. A composition for controlling bacterial growth/colonization comprising:
    an enzyme,
    an anchor molecule coupled to the enzyme to form an enzyme-anchor complex, the anchor being capable of attaching to a substrate proximal to a bacterial colony, wherein the attachment to the substrate permits prolonged retention time of the enzyme-anchor complex where the bacterial colony is present.

2. A composition as claimed in claim 1 wherein the enzyme is selected for its ability to degrade a colonization matrix.

3. A composition as claimed in claim 2 wherein the colonization matrix includes polysaccharides, and the enzyme is selected for its ability to degrade the polysaccharides.

4. A composition as claimed in claim 1 wherein the anchor molecule is capable of attaching to any suitable substrate within an oral cavity.

5. A composition as claimed in claim 4 wherein the anchor molecule attaches to the tooth surface.

6. A composition as claimed in claim 4 wherein the anchor attaches to a pellicle on the tooth surface.

7. A composition as claimed in claim 4 wherein the anchor molecule attaches to a bacterial cell wall.

8. A composition as claimed in claim 4 wherein the anchor molecule is a ligand based molecule designed to mimic exterior cell surfaces of bacteria thereby creating competitive binding between bacteria and the enzyme-anchor complex with the surfaces in the oral cavity.

9. A composition as claimed in claim 1 wherein the surface in the oral cavity is a plaque matrix.

10. A composition as claimed in claim 7 wherein the anchor molecule is a receptor based molecule designed to bind to bacterial attachment sites so that the enzyme-anchor complex can be adsorbed onto bacterial surfaces.

11. A composition as claimed in claim 3 wherein the polysaccharide is glucan.

12. A composition as claimed in claim 3 wherein the polysaccharide is a heterogenous and complex aggregate and mixture of many diverse oligo- and polysaccharides.

13. A composition as claimed in claim 3 wherein the enzyme selected is a hydrolase having hydrolytic activity.

14. A composition as claimed in claim 13 wherein the enzyme is selected from the group consisting of: esterases, for cleaving ester bonds; glycolytic cleavage enzymes, for cleaving bonds that are found in oligo- and polysaccharides; ether bond cleavage enzymes; peptide bond cleavage enzymes where proteins are the substrate (reactant); carbon-nitrogen bond cleavage enzymes where the substrate (reactant) is not a protein; acid anhydride cleavage enzymes; carbon—carbon bond cleavage enzymes; halide bond cleavage enzymes; phosphorus-nitrogen bond cleavage enzymes; sulfurnitrogen bond cleavage enzymes; and carbon-phosphorus bond cleavage enzymes.

15. A composition as claimed in claim 1 wherein the anchor molecule is selected from the group consisting of proteins, protein fragments and polypeptides, being from one or more of the following groups:
    a. naturally-occurring;
    b. naturally-occurring, but modified;
    c. synthetic polypeptides
        i. using naturally occurring amino acids
        ii. using synthetic, non-naturally occurring amino acids, D-amino acids, beta-substituted amino acids, alpha, alphadisubstituted;
    d. charge prevalence; and
        i. cationic (basic amino acids)
        ii. anionic (acidic amino acids)
    e. any combination of the above.

16. A composition as claimed in claim 1 wherein the anchor molecules are saccharides and oligosaccharides, the saccharides and oligosaccharides being selected from the group consisting of:
    a. naturally occurring such as glucose, mannose, galactose, rhamnose, fucose, fructose, sucrose;
    b. naturally occurring amino sugars such as glucosamine, galactosamine, N-actylglucosamine, N-acetylgalactosamine, neuramenic acid, sialic acid;
    c. synthetic or non-naturally occurring saccharides and amino sugars, such as
        i. esters of sugars, sugar-organic acid esters; and
        ii. chemically combined sugars and proteins/polypeptides and synthetic glycoproteins.

17. A composition as claimed in claim 1 wherein the anchor molecules are glycoproteins/proteoglycans, selected from the group consisting of:
    a. naturally occurring such as elastin, lectins,
    b. synthetic such as modified naturally occurring glycoproteins/proteoglycans.

18. A composition as claimed in claim 1 wherein the anchor molecules are glycolipids selected from the group consisting of:
    a. naturally occurring, such as sphingomyelin, cerebroside, gangliosides; and
    b. synthetic or modified natural glycol; lipids through some chemical procedure such as esterification, amidation or similar chemical process.

19. A composition as claimed in claim 1 wherein the anchor molecules are lipoprotein selected from the group consisting of chylomicron, Very Low Density Lipoproteins (VLDL), Low Density Lipoproteins (LDL), and High Density Lipoproteins (HDL).

20. A composition as claimed in claim 1 wherein the anchor molecules are lipids selected from the group consisting of
    a. non-polar, natural or synthetic, such as triglycerides, cholesterol or other plant or animal sterols; and
    b. polar, natural or synthetic such as phospholipids (phosphatidyl serine).

21. A composition as claimed in claim 1 wherein the anchor molecules are cell fragments, cell ghosts or segments or portions of exterior bacterial or animal cell walls or membranes that mimic live and viable bacterial or animal cells for the purpose of securing an enzyme to the surface within the oral cavity.

22. A composition as claimed in claim 1 wherein the anchor molecules are non-biologic, polymeric materials selected from the group consisting of copolymers such as styrene-butadiene polymers.

23. A composition as claimed in claim 1 where the enzyme is α-Glucosidase.

24. A composition as claimed in claim 1 where the enzyme is Dextranase.

25. A composition as claimed in claim 1 wherein the anchor molecule is a basic polypeptide.

26. A composition as claimed in claim 25 where in the basic polypeptide is Lys-Lys-Glu-Lys-Lys.

27. A composition as claimed in claim 1 wherein the anchor molecule is an acidic polypeptide.

28. A composition as claimed in claim 27 wherein the acidic polypeptide is Glu-Glu-Lys-Glu-Glu.

29. A composition as claimed in claim 1 wherein the substrate comprises micelles.

30. A method of controlling bacterial colonization comprising the steps of:

forming an anchor-enzyme complex comprised of an enzyme selected for its ability to degrade at least portion of a colonization matrix, and an anchor, a portion of which is coupled to the enzyme to produce the complex; and selecting the anchor based on the ability of said anchor to attach to a substrate, to thereby increase the retention time of the enzyme-anchor complex in close proximity to the matrix.

31. A method as claimed in claim 30 wherein bacterial colonization is controlled within the oral cavity.

32. A method as claimed in claim 31 wherein the colonization matrix is a plaque matrix, and wherein the plaque matrix comprises polysaccharides.

33. A method of forming a composition for controlling the proliferation of bacterial colonies, the method comprising:

selecting an enzyme based on its ability to degrade the structural component where bacterial colonization occurs;

selecting an anchor molecule based on its ability to couple to the selected enzyme such that the enzyme retains effective enzymatic activity to degrade the structural component, the anchor molecule further being selected for its ability to attach to a substrate proximal the bacterial colonization; and coupling the anchor and enzyme to produce an enzyme-anchor complex.

34. A method as claimed in claim 33 for controlling proliferation of bacterial colonies in the oral cavity.

35. A method of controlling colonization of bacterial plaque in the oral cavity whereby an enzyme specific for degrading plaque is coupled to an anchor selected from the group consisting of cell wall, cell wall fragments, cell fragments and cell ghosts.

* * * * *